United States Patent [19]

Reineke et al.

[11] 4,087,445
[45] May 2, 1978

[54] N-(5,7-DIBROMO-1,3-BENZOXATHIOL-2-YLIDENE)-N-METHYLMETHANAMINIUM BROMIDE, N-(5,7-DIIODO-1,3-BENZOXATHIOL-2-YLIDENE)-N-METHYLMETHANAMINIUM IODIDE AND THEIR PREPARATION

[75] Inventors: Charles E. Reineke; Christian T. Goralski, both of Midland, Mich.

[73] Assignee: The Dow Chemical Company, Midland, Mich.

[21] Appl. No.: 780,889

[22] Filed: Mar. 24, 1977

Related U.S. Application Data

[63] Continuation-in-part of Ser. No. 686,183, May 13, 1976, abandoned.

[51] Int. Cl.² .................... C07D 327/04; A61K 31/40
[52] U.S. Cl. ............................. 260/327 M; 260/608; 260/609 D; 424/276
[58] Field of Search ............... 260/608, 609 D, 327 M

[56] References Cited

U.S. PATENT DOCUMENTS 3,433,803  3/1969  Ottmann et al. ............... 260/327
3,461,168  8/1969  Laufer et al. .................. 260/608
3,476,791  11/1969  Newman et al. ................ 260/455
3,884,931  5/1975  Buttner et al. ................ 260/307 D

FOREIGN PATENT DOCUMENTS 823,251  11/1959  United Kingdom ............ 260/327 M

*Primary Examiner*—Cecilia M. S. Jaisle
*Attorney, Agent, or Firm*—Daniel L. De Joseph; C. Kenneth Bjork

[57] ABSTRACT

N-(5,7-Dibromo-1,3-benzoxathiol-2-ylidene)-N-methylmethanaminium bromide and the analogous diodo iodide, new compounds, are prepared by the thermal rearrangement of O-(2,4,6-tribromophenyl)-N,N-dimethylthiocarbamate and O-(2,4,6-triiodophenyl)-N,N-dimethylthiocarbamate. The first-named compound has antimicrobial utility. Both compounds are useful as starting materials for the preparation of bis-(3,5-dibromo-2-hydroxyphenyl)disulfide and 2,4-diiodo-6-mercaptophenol, respectively, by hydrolysis of the two first-named compounds with methanolic sodium hydroxide. Both the disulfide and the mercaptophenol compounds have antimicrobial utility.

8 Claims, No Drawings

N-(5,7-DIBROMO-1,3-BENZOXATHIOL-2-YLIDENE)-N-METHYLMETHANAMINIUM BROMIDE, N-(5,7-DIIODO-1,3-BENZOXATHIOL-2-YLIDENE)-N-METHYLMETHANAMINIUM IODIDE AND THEIR PREPARATION

REFERENCE TO CO-PENDING APPLICATION

This application is a continuation-in-part of Ser. No. 686,183 filed May 13, 1976, now abandoned.

BACKGROUND OF THE INVENTION

M. S. Newman and H. A. Karnes, J. Org. Chem., 31, 3980 (1966) disclose that when certain O-aryl dialkylthiocarbamates are pyrolyzed, S-aryl dialkylthiocarbamates are obtained in high yields. They also reveal that the so-obtained S-aryl dialkylthiocarbamates are readily hydrolyzed to the corresponding aryl mercaptans to give thiophenols. In reporting on their research, they show that when O-(2,4,5-thrichlorophenyl)-N,N-dimethylthiocarbamate was heated to 220° C, there was obtained the corresponding S-(2,4,5-thrichlorophenyl)-N,N-dimethylthiocarbamate. Nowhere in their report do they show the thermal rearrangement of an O-(2,4,6-tribromophenyl)-N,N-dimethylthiocarbamate or of the analogous triiodophenyl compound to give the compounds herein discovered. The anomolous thermal rearrangement of the starting materials herein to give the product N-(5,7-dibromo-1,3-benzoxathiol-2-ylidene)-N-methylmethanaminium bromide or the corresponding diiodo iodide is nowhere obvious from Newman and Karnes.

SUMMARY OF THE INVENTION

It has now been discovered, in accordance with this invention, that when O-(2,4,6-tribromophenyl)-N,N-dimethylthiocarbamate or the analogous triiodo compound is heated at a temperature of about 170° C for about 24 hours for the former or about 195° C for about 0.5 hour for the latter, that one thereby obtains N-(5,7-dibromo-1,3-benzoxathiol-2-ylidene)-N-methylmethanaminium bromide in the first instance, or N-5,7-diiodo-1,3-benzoxathiol-2-ylidene)-N-methylmethanaminium iodide in the second instance, according to the following equation:

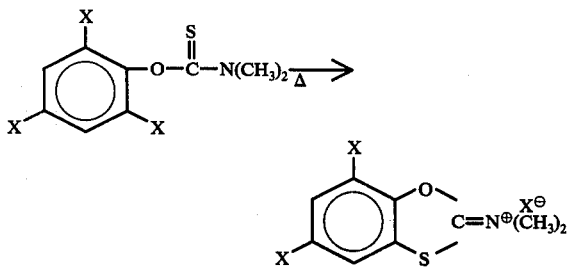

wherein X = Br or I. This was most surprising in view of the publication of Newman and Karnes described earlier concerning their different results with a starting trichloro analog.

In practice, the starting dimethylthiocarbamate compound is heated in a sealed reaction vessel under an inert atmosphere, advantageously nitrogen, at about 170° C for about 24 hours in the case of the tribromo compound and at about 195° C for about 0.5 hour in the case of the triiodo compound. In each case, the solid which forms during the thermal rearrangement is washed with an inert solvent such as carbon tetrachloride or methylene chloride, recovered therefrom by filtration, and again washed with fresh solvent and dried to give product. The product is identified by elemental analysis and by the product of sulfuric acid hydrolysis. The first product, upon hydrolysis with one normal sulfuric acid gave 5,7-dibromo-1,3-benzoxathiol-2-one, identified by infrared and proton nuclear magnetic reasonance spectra and by elemental analysis. The other product of this invention upon hydrolysis with one normal sulfuric acid gave 5,7-diiodo-1,3-benzoxathiol-2-one, identified by infrared and proton nuclear magnetic reasonance spectra and by elemental analysis.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1

Preparation Of N-(5,7-Dibromo-1,3-benzoxathiol-2-ylidene)-N-Methylmethanaminium bromide Fifteen grams (24 m mol) of O-(2,4,6-tribromophenyl)-N,N-dimethylthiocarbamate was heated in a sealed tube under nitrogen at 170° C for 24 hours. During this time, a solid formed in the melt. The tube was cooled, opened, and the contents washed with 75 ml of carbon tetrachloride. The solid which remained insoluble was collected by filtration, washed several times with fresh solvent, and dried to give 2.05 g (13 percent yield) of the subject compound: M.P. 248°–249° C (dec).

Anal. Calcd. for $C_9H_8Br_3NOS$: C, 25.86; H, 1.92; Br, 57.30; N, 3.34; S, 7.66. Found: C, 26.01; H, 2.00; Br, 57.2; N, 3.70; S, 8.10.

The structure was further confirmed by hydrolysis. Five grams (12 m mol) of the title compound in 50 ml of 1N aqueous sulfuric acid was heated on a steam bath for 30 minutes. The mixture was extracted with methylene chloride, the organic layer separated and dried, and condensed in vacuo to give 3.2 g of crude product. Recrystallization from hexane gave 2 g (65 percent) of 5,7-dibromo-1,3-benzoxathiol-2-one: M.P. 104°–106° C; $\nu$ $CCl_4$/max 5.58 (s, sh), 5.63 (s), 6.40 (w), 6.96 (m), 7.12 (w), 7.25 (w), 8.03 (m), 9.96 (s), 11.2 (w) 11.69 (m), and 14.11 (w) μ; nmr ($CCl_4$) δ 7.79 (doublet) and 7.63 (doublet, J = 2.08 Hz).

Anal. Calcd. for $C_7H_2Br_2O_2S$: C, 27.1; H, 0.65; Br, 51.6; S, 10.4. Found: C, 27.3; H, 0.86; Br, 52.4 ± 0.5; S, 10.5

EXAMPLE 2

N-(5,7-Diiodo-1,3-benzoxathiol-2-ylidene)-N-methylmethanaminium iodide

A small pressure tube containing 5 g of O-(2,4,6-triiodophenyl)-N,N-dimethylthiocarbamate was sealed under nitrogen and heated in an oil bath at 195° C for 0.5 hour. The contents gradually melted and then resolidified. The tube was cooled, opened and the contents removed by washing with methylene chloride. The insoluble solid was collected by filtration and dried to give 4.0 g (80 percent) of a tan solid. The solid was washed with methylene chloride and finally with ether. After drying under vacuum there was obtained 2.53 g of the title compound: M.P. 280°–282° C (dec); ν KBr/max 2.91 (m, broad), 5.96 (s), 6.32 (w), 6.42 (w), 6.96 (s), 7.02 (m, sh), 7.28 (w), 7.59 (m), 7.71 (w), 8.01 (s), 8.20 (w), 9.20 (w), 9.36 (w), 11.8 (w), and 14.1 (m) μ.

Anal. Calcd. for $C_9H_8I_3NOS$: C, 19.34; H, 1.44; I, 68.12; N, 2.50; S, 5.74. Found: C, 19.10; H, 1.45; I, 68.8 ± 0.7; N, 2.54; S, 5.89.

The structure was further confirmed by hydrolysis. In an Erlenmeyer flask were placed 1 g (1.8 m mol) of the title compound and 250 ml of 1N sulfuric acid. The flask was warmed on a steam bath for 1.5 hours with occassional stirring. The reaction mixture, which contained a solid, was extracted with chloroform. The chloroform extracts were combined, washed with water, and dried over anhydrous magnesium sulfate. After filtration, the chloroform solution was condensed in vacuo to yield a solid. Recrystallization from methanol gave 0.16 g (22 percent) of 5,7-diiodo-1,3-benzoxathiol-2-one: M.P. 155°–157° C; ν nujol/max 5.73 (s), 8.08 (m), 9.84 (m), 9.99 (m), 11.30 (w), 11.71 (m), 13.55 (m) and 14.18 (w) μ; nmr δ 7.93 (doublet) and 7.58 (doublet J = 1.8 Hz).

Anal. Calcd. for $C_7H_2I_2O_2S$: C, 20.81; H, 0.50; I, 62.83; S, 7.94. Found: C, 21.20; H, 0.68; I, 63.1 ± 0.3; S, 8.10.

In conventional agar Petri dish dilution tests, the compound of Example 1 completely inhibited the growth of the following organisms at the following concentrations in parts per million: S. aureus, 10; B. subtilis, 5; C. albicans N, 50; C. albicans D, 50; C. pelliculosa, 50; A. pullulans, 10; C. ips, 100; T. mentagrophytes, 50; P. chrysogenum, 50; A. fumagatus, 50; A. niger, 50. The compound of Example 1 is a starting material for bis-(3,5-dibromo-2-hydroxyphenyl)disulfide and the compound of Example 2 is a starting material for 2,4-diiodo-6-mercaptophenol. The following examples illustrate the preparation of the disulfide and the mercaptophenol.

EXAMPLE 3

Preparation of bis-(3,5-dibromo-2-hydroxyphenyl)disulfide

Two hundred grams (0.48 mol) of O-(2,4,6-tribromophenyl)-N,N-dimethylthiocarbamate was heated at 170°–175° C under nitrogen with stirring. The disappearance of the starting O-(2,4,6-tribromophenyl)-N,N-dimethylthiocarbamate was complete after 63 hours. An insoluble solid was formed in the melt within the first 4 hours and remained present during the first 45 hours. The solid was absent at the end of the reaction period. The crude product was hydrolyzed by heating it to reflux in methanol containing excess sodium hydroxide by the hydrolysis procedure of Newman e.a., J. Org. Chem. 31, 3980 (1966) to give 170 g. of crude product. Fractional recrystallization from ethanol gave 115 g (69.1 percent yield) of 2,4,6-tribromobenzenethiol: M.P. 113.5°–115.5° C (lit. M.P. 115.5°–115.9° C).

Isolated as the second major product in later fractions was 11 g (8.1 percent yield) of bis-(3,5-dibromo-2-hydroxyphenyl)disulfide: M.P. 122.5°–124° C; ν $CCl_4$/max 2.84 (m), 6.53 (w) 6.94 (s), 7.26 (m), 7.65 (s) 7.97 (w), 8.18 (s), 8.66 (s) 9.14 (w); 9.34 (w), 11.50 (w) and 11.70 (w, sh) μ; nmr ($CDCl_3$) δ 7.79 (doublet, 1H) 7.62 (doublet, 1H, J = 2.4 Hz), and 6.27 (broad singlet, 2H).

Anal. Calcd. for $C_{12}H_6Br_4O_2S_2$: C, 25.5; H, 1.07; Br, 56.3; S, 11.3. Found: C, 25.6; H, 1.28; Br, 55.9 ± 0.3; S, 11.6.

The structure of the disulfide was further proven by reduction to 2,4-dibromophenol with Raney nickel.

EXAMPLE 4

Preparation of 2,4-Diiodo-6-mercaptophenol

An amount of 13 g (23.3 m mol) of N-(5,7-diiodo-1,3-benzoxathiol-2-ylidene)-N-methylmethanaminium iodide was heated at reflux for 4 hours in a mixture of 200 ml of methanol and 50 ml of aqueous 10 percent sodium hydroxide. The reaction mixture was filtered, added to 400 ml of water and acidified with hydrochloric acid. The mixture was extracted with methylene chloride. After drying over anhydrous sodium sulfate, the methylene chloride extract was condensed in vacuo to give 6.1 g (69.4 percent yield) of 2,4-diiodo-6-mercaptophenol: M.P. 177.5°–179.5° C; nmr (DMSO-$d_6$) δ 7.96 (doublet), 7.57 (doublet), and 3.42 (broad singlet).

Anal. Calcd. for $C_6H_4I_2OS$: C, 19.06; H, 1.07; S, 8.48. Found: C, 18.80; H, 1.02; S, 8.2.

The antimicrobial activity of the product of Example 3 was determined by in vitro agar Petri dish dilution tests wherein complete growth inhibition of the following organisms at the following concentrations in parts per million was found: S. aureus, 10; S. typhosa, 50; A. aerogenes, 100; P. aeruginosa, 50; B. subtilis, 5; Klebsiella M, 50; S. marscesens, 50; C. albicans N, 50; C. albicans D, 10; C. pelliculosa, 10; Torulopsis, 10; A. pullulans, 100; C. ips, 50; T. mentagrophytes, 50; P. chrysogenum, 50; A. fumagatus, 50; and A. niger, 50. The compound of Example 4 in similar tests completely inhibited growth of the following organisms at the indicated concentrations in ppm: B. subtilis 5; S. aureus 50.

The starting materials for the products of Examples 1 and 2 were prepared by the procedure of Newman et al., "Organic Synthesis", 51, 139 (1971) as follows:

PREPARATION A

O-(2,4,6-Tribromophenyl)-N,N-dimethylthiocarbamate

Pursuant to the method last cited, 2,4,6-tribromophenol was reacted with N,N-dimethylthiocarbamoyl chloride to give, after recrystallization from ethanol, 227 g (90 percent) of the titular product: M.P. 125°–126° C; ν $CCl_4$/max 3.37 (w), 6.51 (s), 6.95 (s), 7.16 (s), 7.29 (w), 7.76 (s), 8.13 (s), 8.52 (m), 8.90 (m, sh), 9.03 (s, sh), 9.13 (s), 9.34 (w), 11.58 (m), and 13.77 (m) μ; nmr ($CDCl_3$) δ 7.74 (singlet, 2H), 3.49 (singlet, 3H) and 3.41 (singlet, 3H).

Anal. Calcd. for $C_9H_8Br_3NOS$: C, 25.86; H, 1.92; Br, 57.30; N, 3.34. Found: C, 25.9; H, 1.93; Br, 57.4 ± 0.5; N, 3.35.

PREPARATION B

O-(2,4,6-Triiodophenyl)-N,N-dimethylthiocarbamate

Pursuant to the procedure last cited, 2,4,6-triiodophenol was reacted with N,N-dimethylthiocarbamoyl chloride to give a 98 percent yield of the titular product: M.P. 182°–184° C (dec); nmr ($CDCl_3$) δ 3.48 (singlet, 3H), 3.43 (singlet, 3H), and 8.08 (singlet, 2H).

Anal. Calcd. for $C_9H_8I_3NOS$: C, 19.34; H, 1.44; I, 68.12; N, 2.50; S, 5.74. Found: C, 19.40; H, 1.51; I, 68.2 ± 0.2; N, 2.78; S, 5.90.

What is claimed is:

1. A method for making bis-(3,5-dibromo-2-hydroxyphenyl)disulfide by heating in a reaction vessel having an inert atmosphere at about 170° C to substantial completion of reaction O-(2,4,6-tribromophenyl)-N,N-dimethylthiocarbamate to give N-(5,7-dibromo-1,3-benzoxathiol-2-ylidene)-N-methylmethanaminium bromide, hydrolyzing the latter by heating it to reflux in methanol containing excess sodium hydroxide for a time sufficient to form bis-(3,5-dibromo-2-hydroxyphenyl)disulfide and recovering the latter from the reaction medium; or making 2,4-diiodo-6-mercaptophenol by heating in a reaction vessel having an inert atmosphere at about 195° C to substantial completion of reaction O-(2,4,6-triiodophenyl)-N,N-dimethylthiocarbamate to give N-(5,7-diiodo-1,3-benzoxathiol-2-ylidene)-N-methylmethanaminium iodide, hydrolyzing the latter by heating it at reflux in methanol containing excess sodium hydroxide for a time sufficient to form 2,4-diiodo-6-mercaptophenol and recovering the latter from the reaction medium.

2. The method of claim 1 for making bis-(3,5-dibromo-2-hydroxyphenyl)disulfide by heating in a reaction vessel having an inert atmosphere at about 170° C to substantial completion of reaction O-(2,4,6-tribromophenyl)-N,N-dimethylthiocarbamate to give N-(5,7-dibromo-1,3-benzoxathiol-2-ylidene)-N-methylmethanaminium bromide, hydrolyzing the latter by heating it to reflux in methanol containing excess sodium hydroxide for a time sufficient to form bis-(3,5-dibromo-2-hydroxyphenyl)disulfide and recovering the latter from the reaction medium.

3. The method of claim 1 for making 2,4-diiodo-6-mercaptophenol by heating in a reaction vessel having an inert atmosphere at about 195° C to substantial completion of reaction O-(2,4,6-triiodophenyl)-N,N-dimethylthiocarbamate to give N-(5,7-diiodo-1,3-benzoxathiol-2-ylidene)-N-methylmethanaminium iodide, hydrolyzing the latter by heating it at reflux in methanol containing excess sodium hydroxide for a time sufficient to form 2,4-diiodo-6-mercaptophenol and recovering the latter from the reaction medium.

4. The method for making N-(5,7-dibromo-1,3-benzoxathiol-2-ylidene)-N-methylmethanaminium bromide by heating O-(2,4,6-tribromophenyl)-N,N-dimethylthiocarbamate in a reaction vessel under an inert atmosphere at about 170° C to substantial completion of the reaction and recovering N-(5,7-dibromo-1,3-benzoxathiol-2-ylidene)-N-methylmethanaminium bromide.

5. The method for making N-(5,7-diiodo-1,3-benzoxathiol-2-ylidene)-N-methylmethanaminium iodide by heating in a reaction vessel under an inert atmosphere at a temperature of about 195° C O-(2,4,6-triiodophenyl)-N,N-dimethylthiocarbamate to substantial completion of reaction and recovering N-(5,7-diiodo-1,3-benzoxathiol-2-ylidene)-N-methylmethanaminium iodide.

6. A compound of the group consisting of N-(5,7-dibromo-1,3-benzoxathiol-2-ylidene)-N-methylmethanaminium bromide and N-(5,7-diiodo-1,3-benzoxathiol-2-ylidene)-N-methylmethanaminium iodide.

7. The compound of claim 6 which is N-(5,7-dibromo-1,3-benzoxathiol-2-ylidene)-N-methylmethanaminium bromide.

8. The compound of claim 6 which is N-(5,7-diiodo-1,3-benzoxathiol-2-ylidene)-N-methylmethanaminium iodide.

* * * * *

UNITED STATES PATENT AND TRADEMARK OFFICE
CERTIFICATE OF CORRECTION

PATENT NO. : 4,087,445
DATED : May 2, 1978
INVENTOR(S) : Charles E. Reineke and Christian T. Goralski It is certified that error appears in the above–identified patent and that said Letters Patent are hereby corrected as shown below:

Column 1, line 21 "O-(2,4,5-thrichlorophenyl)"
should read -- O-(2,4,5-trichlorophenyl) --;

Column 1, line 23 "S-(2,4,5-thrichlorophenyl)"
should read -- S-(2,4,5-trichlorophenyl) --.

Signed and Sealed this

Tenth Day of October 1978

[SEAL]

Attest:

RUTH C. MASON
Attesting Officer

DONALD W. BANNER
Commissioner of Patents and Trademarks